(12) United States Patent
Derking et al.

(10) Patent No.: US 9,278,945 B2
(45) Date of Patent: Mar. 8, 2016

(54) RELATING TO PROPYLENE OXIDE PURIFICATION

(71) Applicant: SHELL OIL COMPANY, Houston, TX (US)

(72) Inventors: Anke Derking, Amsterdam (NL); Jozef Jacobus Kaandorp, Lumut (BN); Arian Van Mourik, Amsterdam (NL); Manfred Heinz Voetter, Amsterdam (NL); Ying Zhao, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/559,968

(22) Filed: Dec. 4, 2014

(65) Prior Publication Data

US 2015/0158835 A1    Jun. 11, 2015

(30) Foreign Application Priority Data

Dec. 6, 2013    (EP) .................................... 13196095

(51) Int. Cl.
| | | |
|---|---|---|
| *B01D 3/14* | (2006.01) | |
| *B01D 3/00* | (2006.01) | |
| *B01D 3/34* | (2006.01) | |
| *C07D 301/19* | (2006.01) | |
| *B01D 3/32* | (2006.01) | |
| *B01D 3/40* | (2006.01) | |
| *C07D 301/32* | (2006.01) | |

(52) U.S. Cl.
CPC .............. *C07D 301/19* (2013.01); *B01D 3/007* (2013.01); *B01D 3/322* (2013.01); *B01D 3/40* (2013.01); *C07D 301/32* (2013.01)

(58) Field of Classification Search
CPC .......... B01D 3/007; B01D 3/322; B01D 3/40; C07D 301/32; C07D 301/19
USPC ........................ 549/529; 202/158; 203/25, 50
See application file for complete search history.

(56) References Cited

U.S. PATENT DOCUMENTS

| | | | |
|---|---|---|---|
| 3,464,897 A | 9/1969 | Jubin, Jr. et al. | |
| 3,578,568 A | 5/1971 | Washall | |
| 3,909,366 A | 9/1975 | Schmidt et al. | |
| 4,134,797 A * | 1/1979 | Ozero | ............................ 203/75 |
| 4,140,588 A | 2/1979 | Schmidt | |
| 5,006,206 A | 4/1991 | Shih et al. | |
| 5,346,593 A | 9/1994 | Cialkowski et al. | |
| 5,772,854 A | 6/1998 | Nelson et al. | |
| 5,849,938 A | 12/1998 | Rueter et al. | |

FOREIGN PATENT DOCUMENTS

| | | |
|---|---|---|
| EP | 345856 | 12/1989 |
| GB | 1549743 | 8/1979 |

OTHER PUBLICATIONS

European Search Report dated Apr. 3, 2014 for EP Application No. 13196095.7.

* cited by examiner

*Primary Examiner* — T. Victor Oh

(57) ABSTRACT

A method of separating impurities from impure PO, the method comprising distilling impure PO in a distillation zone to provide distillate PO of enhanced purity, wherein heat is provided to the distillation zone by a bottoms reboiler and by an intermediate reboiler, the intermediate reboiler providing heat at a lower temperature than the bottoms reboiler. A suitable distillation system is also disclosed.

14 Claims, 1 Drawing Sheet

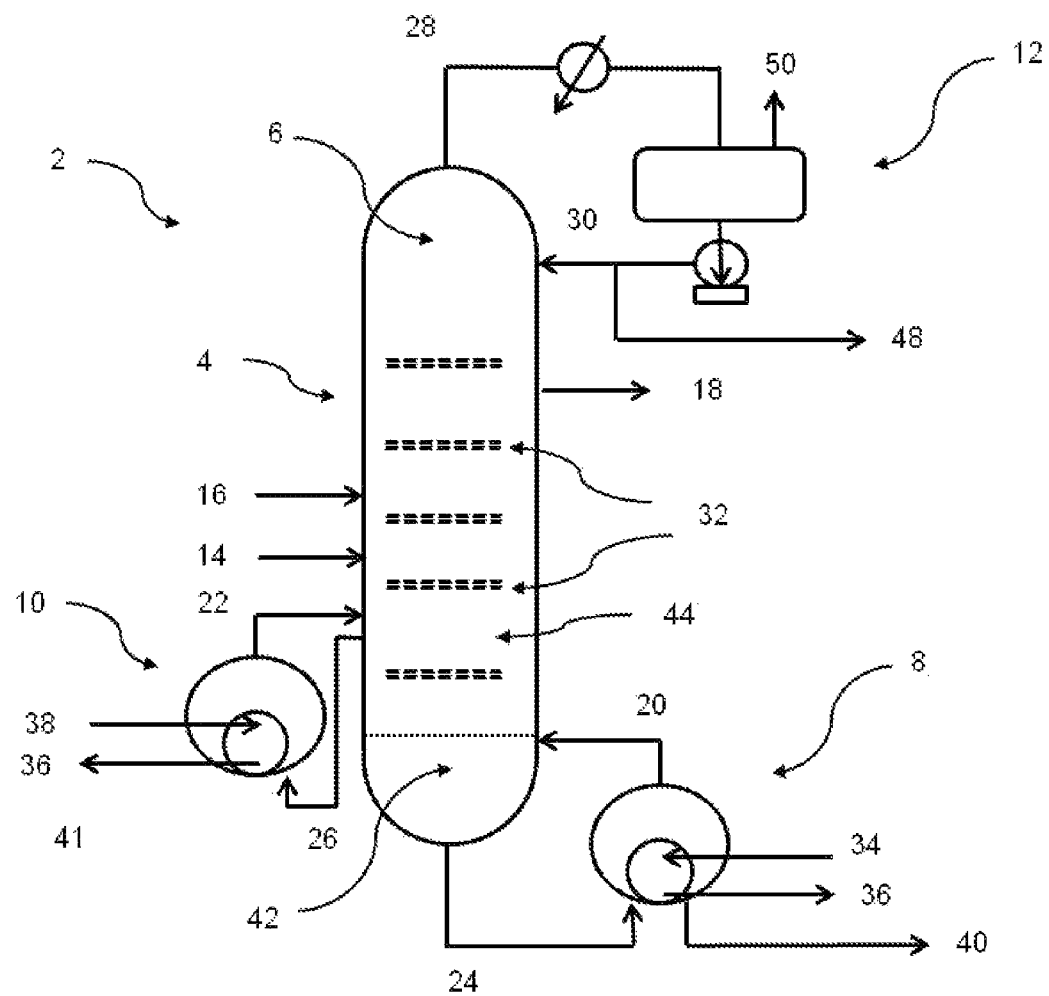

RELATING TO PROPYLENE OXIDE PURIFICATION

This non-provisional application claims the benefit of European Application. No. 13196095.7 filed Dec. 6, 2013 which is hereby incorporated by reference in its entirety.

FIELD OF THE INVENTION

This invention relates to the purification of propylene oxide (PO). In particular, though not exclusively, this invention relates to energy efficient methods and systems for such purification.

BACKGROUND TO THE INVENTION

PO is an essential building block for a variety of chemicals and products. Global production of PO exceeds seven million tonnes per annum.

Direct oxidation of propylene with air or oxygen to form PO tends to provide low yields. PO is therefore most commonly produced with the help of a chemical mediator.

One known process comprises contacting an organic hydroperoxide and propylene with a heterogeneous epoxidation catalyst and withdrawing a product stream comprising PO and an alcohol. A specific organic hydroperoxide that can be used in this epoxidation process is ethylbenzene hydroperoxide (EBHP), in which case the alcohol obtained is 1-phenylethanol. The 1-phenylethanol may be converted into styrene by dehydration. EBHP can be made by reaction of ethylbenzene with oxygen.

Another known process for producing PO is the co-production of PO and methyl tert-butyl ether (MTBE). This process involves similar reaction steps as the above-described styrene/PO production process. In the epoxidation step tert-butyl hydroperoxide is reacted with propylene forming PO and tert-butanol. Tert-butanol is subsequently etherified into MTBE.

Yet another known process comprises the manufacture of PO with the help of cumene. In this process, cumene is reacted with oxygen or air to form cumene hydroperoxide. Cumene hydroperoxide thus obtained is reacted with propylene in the presence of an epoxidation catalyst to yield PO and cumyl alcohol. The latter can be converted into cumene with the help of a heterogeneous catalyst and hydrogen.

Following recent advances, it is also known to produce PO from propylene with the help of hydrogen peroxide as a mediator.

Irrespective of the particular epoxidation process employed, the PO product generally requires purification to remove by-products and impurities. Indeed, for most applications, it is important to reduce impurities in PO to a very low level.

Some by-products of epoxidation processes may be readily separable by distillation. However, epoxidation processes also tend to form by-products and impurities that are more difficult to separate. Taking epoxidation with an organic hydroperoxide as an example, the organic hydroperoxide is predominantly reduced to the corresponding alcohol, which tends to be easy to separate. Also produced, however, are small amounts of other oxygen-containing compounds such as methanol, acetone, acetaldehyde, propionaldehyde and the like, as well as hydrocarbons, which are difficult to separate and often remain as impurities in the PO product even following conventional distillation. Hydrocarbon impurities associated with PO are believed to be propylene derivatives having from 4 to 7 carbon atoms per molecule, especially derivatives having 6 carbon atoms per molecule. The $C_6$ compounds include primarily methyl pentenes and methyl pentanes. Other epoxidation processes also lead to the formation of similarly hard to separate impurities of same or similar structure.

The separation of typical impurities in PO tends to require multiple distillation steps. Furthermore, final purification (or finishing) to high levels of purity by distillation typically requires a column of very substantial size, particularly where the relative volatility of impurities compared to PO is low.

It is known to employ extractive distillation techniques to help separate impurities with a low relative volatility. For example, U.S. Pat. No. 3,909,366 describes the purification of propylene oxide by extractive distillation in the presence of an aromatic hydrocarbon having from 6 to 12 carbon atoms, such as ethyl benzene. A variety of other extractive distillation solvents have also been suggested, including for example cyclic paraffins (see U.S. Pat. No. 3,464,897), lower glycols (see U.S. Pat. No. 3,578,568), water (see U.S. Pat. No. 4,140,588), t-butyl alcohol (see U.S. Pat. No. 5,006,206) and heptane. However, such processes still typically require a column of substantial size.

U.S. Pat. No. 5,772,854 relates to the use of so-called "paired" reboilers, i.e. reboilers connected in series, in the purification of propylene oxide. Specfically, U.S. Pat. No. 5,772,854 provides a process for the purification of a propylene oxide feedstock contaminated with water, methanol and acetone in an extractive distillation column in the presence of an oxyalkylene glycol extractive distillation agent under distillation conditions selected to promote the formation and maintenance of an acetone buffer in the distillation column, wherein a higher boiling (heavier) distillation fraction containing substantially all of the oxyalkylene glycols, water, and acetone is continuously withdrawn from the distillation column and said higher boiling (heavier) distillation fraction is partially vaporized in a first reboiler; the remaining liquid being partially vaporized in a second reboiler and the vapors are recycled to the extractive distillation column.

GB-A-1549743 relates to a method for controlling the heat input to a reboiler section of a distillation column in order to enhance the separation efficiency in achieving the desired end product.

In GB-A-1549743, the "reboiler section" is defined at page 1, lines 62-64 to be that portion of the column below the lowermost tray. Thus, it will be appreciated that the so-called "reboiler section" as described in GB-A-1549743 is a bottom compartment in the distillation column.

The process of GB-A-1549743 comprises withdrawing a liquid bottoms stream from the partially partitioned reboiler section of the distillation column, introducing a first portion of liquid bottoms stream material to a first reboiler, introducing the mixed-phase bottoms stream material produced in said first reboiler to the substantially liquid-free area of the reboiler section, introducing a second portion of liquid bottoms stream material to a second reboiler, introducing mixed-phase bottoms stream material produced in said second reboiler to the same substantially liquid-free area of the reboiler section as the mixed-phase bottoms stream material produced in said first reboiler.

Thus, in process of GB-A-1549743, it will be appreciated that liquid bottoms stream material is withdrawn from the section below the lowermost tray in the distillation column and the mixed phase bottoms streams from the first and second reboilers are also returned to the same location in the distillation column, i.e. below the lowermost tray in the distillation column.

This is clearly shown in the Figure in GB-A-1549743, wherein the liquid bottoms stream material is withdrawn from the so-called reboiler section via outlet port 25, and the mixed phase bottoms streams from the first and second reboilers are returned via inlet ports 30 and 34 also in the reboiler section. The lowermost tray in the Figure is 11.

Purification of PO by distillation, and PO production as a whole, are very energy-intensive, particularly given the substantial size of the columns that are required. It is an object of the invention to provide methods and systems for separating impurities from PO that also permit energy savings to be made.

STATEMENTS OF THE INVENTION

It has now been found that the vapour pressure of PO can be made use of to enable energy savings during PO production and purification.

From a first aspect, the invention resides in a method of separating impurities from impure PO, the method comprising distilling impure PO in a distillation zone to provide distillate PO of enhanced purity, wherein heat is provided to the distillation zone by a bottoms reboiler and by an intermediate reboiler, the intermediate reboiler providing heat at a lower temperature than the bottoms reboiler.

Since the intermediate reboiler provides heat at a lower temperature, a wider range of heat sources can be used in the intermediate reboiler. In particular, the lower temperature requirement enables the use of low-grade heat sources that are often available in the context of PO production and purification and might otherwise go to waste.

In an embodiment, the heat provided by the intermediate reboiler is from a heat source, for example low pressure (LP) steam, having a temperature in the range of from 80 to 180° C., in particular 120 to 140° C. LP steam may, for example, have a pressure in the range of from 1.0 bar abs to 10 bar abs, such as 1.2 bar abs to 3 bar abs.

In an embodiment, the heat provided by the intermediate reboiler is taken directly or indirectly from a process stream cooled as part of a process of producing PO. For example, the LP steam may be flash steam released from a hot condensate. The hot condensate may, for example, be a condensate formed during an epoxidation process for making PO, or during PO distillation. Thus, the heat provided by the intermediate reboiler may be from flash steam generated by cooling of a process stream as part of a process of producing PO. An example of indirect heat from a process stream is heat from a heat pump system.

Advantageously, the LP steam may be freed up by one or more energy saving measures during epoxidation or distillation. It is generally easier to save LP steam than higher grade steam, such as medium pressure (MP) and high pressure (HP) steam. MP steam may, for example, have a pressure in the range of from 10 bar abs to 20 bar abs. HP steam may, for example, have a pressure in the range of from 20 bar abs to 100 bar abs. The method of the invention advantageously enables energy saving measures by providing an effective use of such freed up LP steam.

The distillation zone may be configured in any suitable manner to separate impurities from the impure PO, i.e. to purify PO. To avoid a build-up of impurities in the distillation zone, one or more streams enriched in impurities are typically removed from the distillation zone. The removed impurity stream(s) may comprise one or more of: a bottoms impurity stream, a side-draw impurities stream, and an overhead impurities stream.

In an embodiment, the method comprises refluxing at least part of an overhead vapour exiting the distillation zone. Depending on the design of the distillation zone and the level of impurities to be removed, the reflux ratio may be, for example, in the range of from 1 to 5. As is known in the art, refluxing can assist in enhancing the purity of distillation products. However, in the interest of energy efficiency, it is desirable to minimise the amount of reflux.

It has been appreciated that, in the distillation of PO in particular, temperatures and pressures in the distillation zone may be consistent with both desirably high levels of purification and desirably low reflux whilst facilitating energy savings with the help of an intermediate reboiler.

In an embodiment, to strike a balance between low distillation zone temperatures and other process considerations, the pressure in the distillation zone may be maintained in the range of from 1 bar abs to 10 bar abs, preferably in the range of from 1.5 bar abs to 5 bar abs, more preferably in the range of from 2 bar abs to 3 bar abs.

The temperatures in the distillation zone are affected by the operation and placement of the bottoms reboiler and the intermediate reboiler. In an embodiment, the bottoms reboiler inputs heat to a bottoms region of the distillation zone and the intermediate reboiler inputs heat to an upper region of the distillation zone. The upper region may be taken as any part of the distillation zone above the level at which heat is input by the bottoms reboiler. Correspondingly, the bottoms region may be taken as the remainder of the distillation zone, i.e. the region at and below the level at which the bottoms reboiler inputs heat.

Advantageously, the temperature profile of the distillation zone may facilitate energy savings. The energy saving opportunities resulting from the provision of heat by both the bottoms reboiler and the intermediate reboiler are generally enhanced where the distillation zone is configured such that: (i) the upper region comprises a plurality of trays conforming to a relatively flat temperature profile; and (ii) there is a sharp temperature difference between the bottoms region and said plurality of trays in the upper region.

An upper region with a plurality of trays conforming to a relatively flat temperature profile presents an opportunity to provide significant heat at a relatively constant temperature. Due to the vapour pressure and the purity of PO in this region of the zone, the relatively constant temperature may be such that it permits use of lower grade heat sources. Temperatures and pressures may hence be controlled to provide a good balance between product purity and energy saving opportunities.

In an embodiment the upper region of the distillation zone comprises a plurality of consecutive trays having tray temperatures that differ by at most 40° C., preferably at most 30° C., more preferably at most 20° C. Suitably, said plurality of trays may comprise at least 10 theoretical trays, preferably at least 20 theoretical trays, more preferably at least 30 theoretical trays. In an embodiment, the temperature of said plurality of trays is in the range of from 50 to 120° C., preferably in the range of from 55 to 100° C., more preferably in the range of from 60 to 90° C. Advantageously, said plurality of trays may be located above a heat input of the intermediate reboiler.

A sharp temperature difference between the bottoms region and trays conforming to a flat temperature profile in the upper region can help to minimise efficiency trade-offs inherent in providing heat from both an intermediate and a bottoms reboiler. In particular, a sharp temperature difference enables the intermediate reboiler to be placed closer to the bottoms reboiler, thereby minimising the distillation zone between the bottoms reboiler and the intermediate reboiler, where a reduced share of reboiler duty of the bottoms reboiler has an impact. In an embodiment, at least one reference tray of the upper region has a temperature which is at least 30° C., preferably at least 50° C., more preferably at least 70° C. lower than the maximum tray temperature of the bottoms region. Preferably the reference tray may be a lowermost one of a plurality of consecutive trays of the upper region having tray temperatures that differ by at most 40° C., preferably at most 30° C., more preferably 20 ° C., e.g. as defined hereinabove. Preferably, there may be at most 30 theoretical trays between the reference tray and the bottoms region, more preferably at most 15 theoretical trays or at most 10 theoretical trays. In an embodiment, the number of theoretical trays between the reference tray and the bottoms region is at most 40%, preferably at most 20% or even at most 10% of the overall number of theoretical trays in the distillation zone.

The intermediate reboiler may provide heat to any part of the upper region of the distillation zone. Placement low in the upper region and/or below a plurality of trays with a relatively flat temperature profile is preferred. Advantageously, the intermediate reboiler may provide heat below an impure PO inlet of the distillation zone.

In an embodiment, the method comprises drawing distillation mixture from the upper region of the distillation zone into the intermediate reboiler, heating the mixture by heat exchanging with a heat source or medium, and returning the mixture to the distillation zone, typically as vapour or a combination of vapour and liquid. The particular position of the intermediate reboiler, i.e. its draw (or take off) and return, may be chosen, for example, based on available heat sources and the particular temperature profile desired in the distillation zone.

Advantageously, the intermediate reboiler may input heat into the distillation zone at one or more trays of the upper region having a tray temperature which is at least 30° C., preferably at least 50° C., more preferably at least 70° C. lower than the maximum temperature of the bottoms region, i.e. for example a reference tray as defined hereinabove. In an embodiment, the intermediate reboiler advantageously inputs heat at or below a lowermost one of a plurality of trays of the upper region having tray temperatures that differ by at most 40° C., preferably at most 30° C., more preferably at most 20° C., e.g. as defined hereinabove above.

In an embodiment, the method comprises drawing distillation mixture into the intermediate reboiler from a tray of the distillation zone having a temperature in the range of from 50 to 120° C., preferably in the range of from 55 to 100° C., more preferably in the range of from 60 to 90° C., heating the mixture and returning the mixture to the distillation zone.

In an embodiment, the method comprises drawing distillation mixture into the intermediate reboiler from the distillation zone, heating the mixture and returning the heated mixture to a tray of the distillation zone having a temperature in the range of from 50 to 120° C., preferably in the range of from 55 to 100° C., more preferably in the range of from 60 to 90° C.

In an embodiment, the distillation mixture is drawn from and returned above the same tray of the distillation zone.

The intermediate reboiler assumes a share of overall reboiler duty for the distillation zone and is therefore able to reduce the duty of the bottoms reboiler. In an embodiment heat is provided to the distillation zone by a plurality of intermediate reboilers, e.g. at least two, or at least three intermediate reboilers. In an embodiment, the intermediate reboiler(s) may assume at least 10%, preferably at least 25%, more preferably at least 50% of overall reboiler duty. In an embodiment, the intermediate reboiler(s) assume(s) at most 80%, preferably at most 70% of reboiler duty.

In an embodiment, the or each intermediate reboiler has a duty of at least 2 megawatts (MW), preferably at least 4 MW, more preferably at least 7 MW. In an embodiment, the or each intermediate reboiler has duty of at most 12 MW, such as at most 10 MW.

The bottoms reboiler retains the remaining share of overall reboiler duty. In an embodiment, heat is provided to the distillation zone by a plurality of bottoms reboilers, e.g. at least two, or at least three bottoms reboilers. In an embodiment, the or each bottoms reboiler has a duty in the range of from 4 MW to 15 MW, such as in the range of from 5 to 10 MW.

In an embodiment, the PO is distilled by extractive distillation. Accordingly, distilling the impure PO may comprise extractively distilling the impure PO with an extractive distillation solvent. In an embodiment, the method comprises feeding impure PO into the distillation zone, introducing a separate feed of extractive distillation solvent into the zone at a level above the impure PO feed, removing purified PO as a distillate from the zone, and removing extractive distillation solvent enriched in impurities as bottoms from the zone.

Advantageously, extractive distillation may enhance energy saving opportunities by facilitating a sharp temperature difference between the bottoms region of the distillation zone and trays of the upper region conforming to a relatively flat temperature profile. When using an extractive distillation solvent a relatively high bottom temperature may be required to boil up the solvent, enhancing energy saving opportunities in accordance with the invention.

In an embodiment, the extractive distillation solvent has a boiling point of at least 70° C., e.g. at least 100° C. In an embodiment, the extractive distillation solvent is selected from aromatic hydrocarbons, cyclic paraffins, glycols, water and t-butyl alcohol. Preferably, the extractive distillation solvent is an aromatic hydrocarbon having 6 to 12 carbon atoms. Even more preferably, the extractive distillation solvent is an alkyl benzene, in particular ethyl benzene.

The relative feed rate of the extractive distillation solvent with respect to impure PO may be determined by those skilled in the art based in the particular nature of the feeds and the configuration of the distillation zone. In an embodiment, the solvent to PO feed ratio may be in the range of from 0.1 to 3, preferably in the range of from 0.2 to 1.

The impure PO may be obtained by any suitable process. In an embodiment, the impure PO is obtained by epoxidation of propylene in the presence of a chemical mediator such as a peroxide, e.g. as described hereinabove. Preferably, the PO is obtained by contacting a peroxide, especially an organic hydroperoxide, and propylene with a heterogeneous epoxidation catalyst. A product stream comprising PO and an alcohol may be withdrawn and optionally subjected to at least one preliminary distillation to recover the impure PO as a distillate. Most preferably, the organic hydroperoxide is ethylbenzene hydroperoxide. Suitable heterogeneous epoxidation catalysts are known in the art. Preferably, the epoxidation catalyst may comprise titanium in chemical combination with a solid silica and/or inorganic silicate. An example of such a catalyst and its use in epoxidation is described in EP0345856B1.

The impure PO input into the distillation zone comprises a substantial amount of PO. In an embodiment, the impure PO comprises in the range of from 90 to 99.9% w/w PO, preferably at least 95% w/w PO.

In an embodiment, the impure PO may comprise in the range of from 0.1 to 10% w/w of one or more impurities, preferably at most 5% w/w of one or more impurities. The impurities may, for example, comprise or consist of water, one or more alcohols, aldehydes, ketones, or combinations thereof. In an embodiment, the impurities comprise or consist of one or more of propionaldehyde, acetaldehyde, acetone, methanol and propylene derivatives having from 4 to 7 carbon atoms per molecule, especially derivatives having 5 or 6 carbon atoms per molecule. However, other impurities may also be present.

In an embodiment, the impure PO comprises propionaldehyde in an amount of at least 250 ppm wt, e.g.

at least 800 ppm or at least 1000 ppm. In an embodiment, the impure PO comprises propionaldehyde in an amount up to 5000 ppm e.g. in an amount up to 3000 ppm.

In an embodiment, the impure PO comprises propylene derivatives having from 4 to 7 carbon atoms per molecule, especially derivatives having 5 or 6 carbon atoms per molecule, in an amount of at least 50 ppm wt, e.g. at least 75 ppm. In an embodiment, the impure PO comprises such derivatives in an amount up to 1000 ppm, e.g. up to 200 ppm.

In an embodiment, the impure PO comprises acetaldehyde in an amount of at least 0.1 ppm wt, e.g. at least 3 ppm. In an embodiment, the impure PO comprises acetaldehyde in an amount up to 40 ppm, e.g. up to 20 ppm.

The distillate PO of enhanced purity has a lower concentration of impurities than the impure PO and is typically obtained as a side draw from the distillation zone. In an embodiment, the amount of one or more impurities in the distillate PO is reduced by at least 20% w/w, preferably by at least 50% w/w, more preferably by at least 90% w/w.

In an embodiment, the distillate PO comprises at least 99.5% w/w PO, preferably at least 99.995% w/w PO. In an embodiment, the distillate PO comprises less than 0.5% w/w of impurities, preferably less than 0.005% w/w of impurities.

In an embodiment, the distillate PO comprises propionaldehyde in an amount of less than 200 ppm wt, e.g. less than 100 ppm or less than 50 ppm.

In an embodiment, the distillate PO comprises propylene derivatives having from 4 to 7 carbon atoms per molecule, especially derivatives having 5 or 6 carbon atoms per molecule, in an amount of less than 100 ppm wt, e.g. less than 75 ppm or less than 50 ppm.

In an embodiment, the distillate PO comprises acetaldehyde in an amount of less than 20 ppm wt.

The method is preferably carried out in continuous fashion, i.e. by keeping the distillation zone in a substantially steady state for a prolonged period, e.g. of at least 12 hours. Further details of the method, such as, for example, feed rates, may be readily determined by those skilled in the art.

The distillation zone may in principle be implemented with, or defined by, any suitable apparatus or hardware.

From a second aspect, the invention resides in a distillation system for separating impurities from impure PO, the system comprising:

a structure defining a distillation zone having an inlet for impure PO, a distillate outlet for purified PO, and one or more outlets for streams enriched in impurities;

a bottoms reboiler for providing heat to the distillation zone at a first temperature; and an intermediate reboiler for providing heat to the distillation zone at a second temperature lower than the first temperature.

Advantageously, the distillation system may be arranged for use in or according to any of the methods described hereinabove.

The structure defining the distillation zone may be implemented or arranged using components known in the art of PO distillation, e.g. walls, inlets, outlets, conduits, trays and/or packing material. The structure may comprise a column or a plurality of columns.

In an embodiment, the distillation zone comprises at least 30 theoretical trays, preferably at least 40 theoretical trays. Suitably the overall number of theoretical trays may be up to 100 trays, for example up to 80 trays.

In an embodiment, the distillation zone comprises at most 30 theoretical trays between a bottoms reboiler input and an intermediate reboiler input, more preferably at most 15 theoretical trays or at most 10 theoretical trays. In an embodiment, the number of such theoretical trays is less than 40% of the overall number of trays, preferably less than 20% or even 10% of the overall number of trays.

In an embodiment, the distillation zone comprises at least 10 theoretical trays above the intermediate reboiler input, preferably at least 20 theoretical trays.

In an embodiment, the theoretical trays are implemented by column trays and/or random or structured packing.

In an embodiment, the bottoms reboiler is arranged to input heat to a bottoms region of the distillation zone, and the intermediate reboiler is arranged to input heat to an upper region of the distillation zone. The bottoms region and the upper region may be defined as hereinabove. Therefore, in other words, the intermediate reboiler is positioned above the bottoms reboiler in such an arrangement.

The intermediate reboiler may be any heat exchanger or heater capable of transferring heat from a heat source to the upper region of the distillation zone. The intermediate reboiler may comprise or define a first flow path for drawing liquid mixture from the upper region of the distillation zone into the reboiler, heating means for heat exchanging or heating the liquid mixture with the heat source, and a second flow path for returning the heated mixture to the distillation zone. The intermediate reboiler may comprise a pump to assist circulation, or may rely on natural circulation. Advantageously, the intermediate reboiler may be of the thermosyphon type. However, other reboiler types are known to the skilled person.

The bottoms reboiler may be any heat exchanger or heater capable of transferring heat from a heat source to the bottoms region of the distillation zone. The bottoms reboiler may comprise or define a first flow path for drawing liquid mixture from the bottoms region of the distillation zone into the reboiler, heating means for heat exchanging or heating the liquid mixture with the heat source, and a second flow path for returning the heated mixture to the distillation zone. The bottoms reboiler may comprise a pump to assist circulation, or may rely on natural circulation. Advantageously, the bottoms reboiler may be of the thermosyphon or kettle type. However, other reboiler types are known to the skilled person.

The distillation zone may be defined exclusively by the structure, or by the structure in combination with one or more of the reboilers.

The one or more outlets for streams enriched in impurities may include, for example, one or more of a bottoms impurity outlet, a side-draw impurities outlet, and an overhead impurities outlet.

In an embodiment, the system may further comprise a reflux component for recycling overhead product to the distillation zone.

To cater for extractive distillation, the distillation zone may comprise an inlet for extractive distillation solvent located above the inlet for impure PO, and a bottoms outlet for extractive distillation solvent enriched in impurities.

In an embodiment, the bottoms reboiler of the system takes the form of a bottoms stripper taking a bottoms flow as feed from a main distillation column of the system and returning overhead vapour of the stripper to the main distillation column. In this embodiment, the intermediate reboiler may be a bottoms reboiler of the main distillation column.

From a third aspect, the invention resides in a method of producing PO, the method comprising contacting a peroxide and propylene with an epoxidation catalyst to obtain PO, for example as described anywhere hereinabove, and separating impurities from the PO by a method according to the first aspect of the invention and/or with a distillation system according to the second aspect of the invention.

Throughout the description and claims of this specification, the words "comprise" and "contain" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Other features of the invention will become apparent from the following specific description of an embodiment. Generally speaking the invention extends to any novel one, or any novel combination, of the features disclosed in this specification (including any accompanying claims and drawings). Thus features, integers, characteristics, or compounds described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

Where upper and lower limits are quoted for a property then a range of values defined by a combination of any of the upper limits with any of the lower limits may also be implied.

SPECIFIC DESCRIPTION

In order that the invention may be more readily understood, reference will now be made, by way of example, to the accompanying FIG. 1 showing a schematic view of a distillation column in accordance with one embodiment of the invention.

With reference to FIG. 1, a distillation system 2 for separating impurities from impure PO comprises a column structure 4 of walls and internals defining a distillation zone 6, a bottoms reboiler 8, an intermediate reboiler 10, and a reflux system 12.

The structure 4 of the system 2 defines an impure PO inlet 14 and an extractive distillation solvent inlet 16 into the distillation zone 6, and a purified PO outlet 18 from the distillation zone 6. Also defined are inlets 20, 22 and outlets 24, 26 for the bottoms reboiler 8 and the intermediate reboiler 10, as well as an overhead outlet 28 and a reflux inlet 30. From bottom to top of the column 2, the outlet 24 to the bottoms reboiler 8 is lowermost, followed by the inlet 20 from the bottoms reboiler 8, the outlet and inlet 26, 22 to and from the intermediate reboiler 10 which are at the same level, the impure PO inlet 14, the extractive solvent inlet 16, the purified PO outlet 18, the reflux inlet 30, and the overhead outlet 28.

Column trays 32 are provided between the inlets and outlets to aid distillation in the distillation zone 6. In particular, the column structure 2 comprises eleven theoretical trays between the inlet 20 from the bottoms reboiler and the outlet and inlet 26, 22 of the intermediate reboiler, nine theoretical trays between the outlet and inlet 26, 22 of the intermediate reboiler and the impure PO inlet 14, forty-five theoretical trays between the impure PO inlet 14 and the extractive distillation solvent inlet 16, six theoretical trays between the extractive distillation solvent inlet and the purified PO outlet 18 and six theoretical trays between the purified PO outlet and the overhead outlet 28 and reflux inlet 30. The theoretical trays are implemented in practice using conventional column trays but can also be executed as random or structured packing in other embodiments.

The bottoms reboiler 8 is a thermosyphon reboiler powered by an input of relatively high temperature steam 34, e.g. HP or MP steam, with condensate 36 being withdrawn. To provide an impurity outlet for the distillation zone 6, the bottoms reboiler 8 comprises a bleed 40 for bleeding off liquid components, in particular extractive distillation solvent enriched in impurities.

The intermediate reboiler 10 is a thermosyphon reboiler powered by an input of lower temperature steam 38, e.g. LP steam, with condensate 36 being withdrawn.

In operation, impure PO and ethyl benzene as extractive distillation solvents are supplied to the distillation zone via their inlets. The impure PO comprises approximately 99.6% wt PO, about 3500 ppm wt propionaldehyde, about 250 pm wt propylene derivatives having from 4 to 7 carbon atoms per molecule, and a balance of other impurities.

The bottoms reboiler 8 inputs heat into a bottoms region 42 of the distillation zone 6. The intermediate reboiler 10 inputs heat into a remaining, upper region 44 of the distillation zone 6. The intermediate reboiler represents about 70% of the overall reboiler duty. The remainder of the reboiler duty is assumed by the bottoms reboiler 8.

The provided heat results in distillation within the distillation zone. Distillate PO 18 of improved purity, with the concentration of impurities reduced by more than 95%, is withdrawn from the distillation zone, as is a bottoms bleed 40 of ethyl benzene enriched in impurities. The reflux system 12 of the reboiler, which includes a liquid impurity outlet 48 and vent 50, is controlled accordingly.

The column 2 is operated such that that all the consecutive trays between the inlet 22 from the intermediate reboiler and the purified PO outlet 18 conform to a flat temperature profile, i.e. have tray temperatures lying within 20° C. In particular, the temperature of these trays is maintained in the range of from 50° C. to 70° C. for the specific operating pressure considered. The intermediate reboiler 10 is thus able to operate on LP steam 38 having a temperature of about 130° C. and a pressure of about 2.5 bar abs. Such low grade steam 38 may result from one or more energy saving measures elsewhere.

By contrast, the maximum temperature of the bottoms region 42 is about 170° C. To provide this temperature, the bottoms reboiler is operated on MP steam 34 having a temperature of about 220° C. and a pressure of about 18 bar abs.

The ability to use LP steam 34 in the intermediate reboiler 10 lowers the overall demand for HP steam for the bottoms reboiler 8. Furthermore, with the number of theoretical trays between the input of the bottoms reboiler 8 and the input of the intermediate reboiler 10 being low, the detrimental effect of the intermediate reboiler 10 supplying some heat further up the column 2 is minimised.

It will be appreciated by those skilled in the art that a great number of modifications could be made to the column 2 without departing from the invention. For example the feeds, trays and column design as a whole could be varied whilst still accommodating the bottoms and intermediate reboilers. In one embodiment, the column is modified to be a conventional distillation column operating without extractive distillation solvent to accommodate an impure PO feed calling for such a setup.

In another embodiment an existing column, having a bottoms reboiler only, is extended with an additional bottoms stripper with bottom reboiler, which takes the function of the original bottoms reboiler by taking the original bottoms flow as feed and returning its overhead vapour in the original column. The distillation zone of the column is thus extended downwards. The original bottoms reboiler is converted to use low level heat and acts as an intermediate reboiler in the new configuration.

We claim:

1. A method of separating impurities from impure propylene oxide, the method comprising distilling impure propylene oxide in a distillation zone to provide distillate propylene oxide of enhanced purity, wherein heat is provided to the distillation zone by a bottoms reboiler and by an intermediate reboiler, the intermediate reboiler providing heat at a lower temperature than the bottoms reboiler.

2. The method of claim 1, wherein the heat provided by the intermediate reboiler is from a heat source having a temperature in the range of from 80° C. to 180° C.

3. The method of claim 1, wherein the heat provided by the intermediate reboiler is taken directly or indirectly from a process stream cooled as part of a process of producing propylene oxide.

4. The method of claim 3, wherein the heat provided by the intermediate reboiler is from flash steam generated by cooling of a process stream as part of a process of producing propylene oxide.

5. The method of claim 1, wherein the bottoms reboiler inputs heat to a bottoms region of the distillation zone and the intermediate reboiler inputs heat to an upper region of the distillation zone.

6. The method of claim 5, wherein the upper region of the distillation zone comprises a plurality of at least 10 consecutive theoretical trays having tray temperatures that differ by at most 40° C.

7. The method of claim 6, wherein the temperature of said plurality of trays is in the range of from 50 to 120° C.

8. The method of claim 5, wherein the intermediate reboiler inputs heat at a reference tray of the upper region having a temperature which is at least 50° C. lower than the maximum temperature of the bottoms region, the reference tray being a lowermost one of a plurality of at least 10 consecutive theoretical trays in the upper region, said plurality of trays having tray temperatures that differ by at most 40° C.

9. The method of claim 1, wherein the intermediate reboiler, or a combination of intermediate reboilers, assumes at least 25% of overall reboiler duty.

10. The method of claim 1, wherein the impure propylene oxide is distilled by extractive distillation.

11. The method of claim 1, wherein the distillate propylene oxide comprises at least 99.5% w/w propylene oxide.

12. A distillation system for separating impurities from impure propylene oxide, the system comprising:
a structure defining a distillation zone having an inlet for impure propylene oxide, a distillate outlet for purified propylene oxide, and one or more outlets for streams enriched in impurities;
a bottoms reboiler for providing heat to the distillation zone at a first temperature; and
an intermediate reboiler for providing heat to the distillation zone at a second temperature lower than the first temperature.

13. The distillation system of claim 12 wherein the distillation zone comprises: at most 15 theoretical trays between a bottoms reboiler input and an intermediate reboiler input into the distillation zone; and at least 10 theoretical trays above the intermediate reboiler input.

14. The distillation system of claim 12, wherein the distillation zone comprises an inlet for extractive distillation solvent located above the inlet for impure propylene oxide, and a bottoms outlet for extractive distillation solvent enriched in impurities.

* * * * *